United States Patent
Chladek

(10) Patent No.: US 12,042,418 B2
(45) Date of Patent: Jul. 23, 2024

(54) ORTHOTIC SYSTEM FOR STABILIZING AN ANKLE AND A FOOT

(71) Applicant: Noel J. Chladek, Des Moines, IA (US)

(72) Inventor: Noel J. Chladek, Des Moines, IA (US)

(*) Notice: Subject to any disclaimer, the term of this patent is extended or adjusted under 35 U.S.C. 154(b) by 0 days.

(21) Appl. No.: 16/791,439

(22) Filed: Feb. 14, 2020

(65) Prior Publication Data

US 2021/0251792 A1     Aug. 19, 2021

(51) Int. Cl.
*A61F 5/01*     (2006.01)

(52) U.S. Cl.
CPC .... *A61F 5/0127* (2013.01); *A61F 2005/0167* (2013.01)

(58) Field of Classification Search
CPC .... A61F 5/0113; A61F 5/0123; A61F 5/0127; A61F 5/37; A61F 5/0111; A61F 5/04; A61F 5/0109; A61F 2005/0165; A61F 2005/0167; A61F 2005/0179; A61F 2005/0158; A61F 2005/0197; A61F 2002/5066; A61H 1/0262; A61H 1/024; A61H 1/0244; A61H 1/0266; A61H 1/0237; A61H 3/00; A61H 2201/5056; A61H 2201/1642; A61H 2201/163; A61H 2201/1238; A61H 2201/1246; A61H 2201/0192; A61H 2201/165; A61H 2201/5071; A61H 2201/0157
USPC ..................................................... 602/27, 28
See application file for complete search history.

(56) References Cited

U.S. PATENT DOCUMENTS

| | | | | |
|---|---|---|---|---|
| 5,038,762 | A * | 8/1991 | Hess | A43B 7/1495 602/27 |
| 5,226,875 | A * | 7/1993 | Johnson | A43B 7/20 36/114 |
| 5,317,820 | A * | 6/1994 | Bell | A43B 7/20 36/114 |
| 5,759,168 | A * | 6/1998 | Bussell | A61F 5/0111 602/23 |
| 6,245,035 | B1 * | 6/2001 | Schrijver | A61F 5/0111 602/65 |
| 2006/0264795 | A1 * | 11/2006 | Christensen | A61F 5/0111 602/23 |
| 2012/0238928 | A1 * | 9/2012 | Buethorn | A61F 5/14 602/27 |
| 2015/0320581 | A1 * | 11/2015 | Causse | A61F 5/0127 602/28 |
| 2017/0165095 | A1 * | 6/2017 | Romo | A61F 5/0111 |
| 2017/0196720 | A1 * | 7/2017 | Hassel | A61F 5/0113 |

* cited by examiner

*Primary Examiner* — Ophelia A Hawthorne
*Assistant Examiner* — Michael Milo
(74) *Attorney, Agent, or Firm* — Brett J. Trout

(57) ABSTRACT

The present disclosure is directed to an improved orthosis system for stabilizing an ankle and a foot of a user against undesired orientations and having a calf brace and a foot brace. The system uses first and second risers coupled to a foot section using a construction and configuration whereby the more the risers are deflected relative to the foot section, the more the system bias the risers toward their initial orientation relative to the foot section. To increase lateral stability, the first riser curves forward around at least a portion of a lateral malleolus of a user's ankle, while the second riser curves rearward and around at least a portion of a medial malleolus of the user's ankle. To increase forward and rearward stability, the foot section extends across at least half the length of the sole of a user's foot.

7 Claims, 10 Drawing Sheets

ORTHOTIC SYSTEM FOR STABILIZING AN ANKLE AND A FOOT

TECHNICAL FIELD

The following disclosure relates generally to orthoses and, more particularly, to an orthosis system for stabilizing an ankle and a foot of a user against undesired orientations.

BACKGROUND

Orthotic devices are well known in the art. When a user loses partial or complete control of a muscle group, the structure of the joints of the foot and ankle can be compromised, orthoses may compensate for some or all of the missing structure to return function. When used for rehabilitation of a user having weak or absent anterior and/or posterior calf muscle group function, or experiences a breakdown of the ligaments, an orthosis may provide the user's leg with missing support and align the user's foot as the user walks or stands.

One drawback associated with prior art orthoses is that the further plastic supports used in such devices are either too rigid, or are too flexible, the point where the more they are deflected away from their initial position during movement by a user, the easier it becomes to bend these plastic supports even farther. This means that these prior art devices are least able to provide support when they are most needed, that is, when they are excessively deflected from their initial position. As a result, such prior art supports are often overbuilt to reduce deflection from their initial position, which would otherwise make the supports more and more susceptible to extreme bending as the supports are deflected more and more from their initial position. This overbuilding may lead to such prior art devices having a rigid positioning inhibiting function of the user's foot and ankle with the use of the orthosis.

Another drawback associated with the prior art is the limited ability of prior art ankle supports to rebound energy to the foot of the user during ambulation. Typically, the majority of prior art systems is located below the ankle. This orientation provides less leverage of upward supports relative to a footplate, thereby reducing the efficiency with which energy may be rebounded to the footplate as the upward supports are biased forward and backward during ambulation. Such prior art orthoses stabilize the ankle by limiting motion of the ankle, reducing the rebound of energy from the orthosis toward ambulation and reducing the movement of the user's ankle necessary for optimal rehabilitation.

Prior art systems often use small footplates extending across only a small portion of the sole of a user's foot. Smaller footplates provide lateral stabilization of a user's foot and smaller footplates reduce the material and manufacturing costs of such prior art systems. One drawback associated with such small footplates is their reduced capacity to provide a user with the desired amount of forward and rearward stabilization.

The present invention improves upon prior art orthosis systems for stabilizing an ankle and a foot by using a construction and configuration of uprights to avoid the reduced leverage and undesired bending issues of the prior art. The present invention also improves upon prior art orthosis systems for stabilizing an ankle and a foot by using a construction and configuration of a footplate to reduce the forward and rearward instability of prior art systems.

SUMMARY OF THE DISCLOSED SUBJECT MATTER

The system of the present disclosure is directed to an improved orthosis system for stabilizing an ankle and a foot of a user against undesired orientations and having a calf brace and a foot brace. In an illustrative implementation, an orthosis is provided having a first and second riser coupled to a foot section using a construction and configuration whereby the risers and foot section bias the orthosis toward the predetermined orientation the more the risers are forced away from the predetermined orientation.

At least one aspect of the present disclosure is an orthosis is provided having a resin-impregnated carbon fiber first and second riser coupled to a resin-impregnated carbon fiber foot section. In some implementations, the first riser is provided with a curved section that extends forward around at least a portion of a lateral malleolus of a user's foot, while the second riser is provided with a supplemental curved section that extends rearward around at least a portion of a medial malleolus of a user's foot. In some implementations, the foot section extends across at least half the length of the sole of a user's foot.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DESCRIPTION OF EMBODIMENTS

Overview

An orthosis system for supporting the leg and foot of a user having reduced support and/or flexibility in their ankle and/or foot. The orthosis resists a user's leg from bending more than a predetermined angle relative to a footplate of the orthosis and rebounds energy to the user during ambulation. The orthosis system may be used to support *varus* deformities as well as valgus deformities. The orthosis system may also be used to support a user's leg and foot against undesired plantar flexion and dorsal flexion.

The Components

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, resins, and fabrics have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first riser could be termed a second riser, and, similarly, a second riser could be termed a first riser, without departing from the scope of the present invention. The first riser and the second riser are both risers, but they are not the same riser.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof. As used herein, the term "if" may be construed to mean "when" or "upon" or "in response to" depending on the context.

Figure 1:
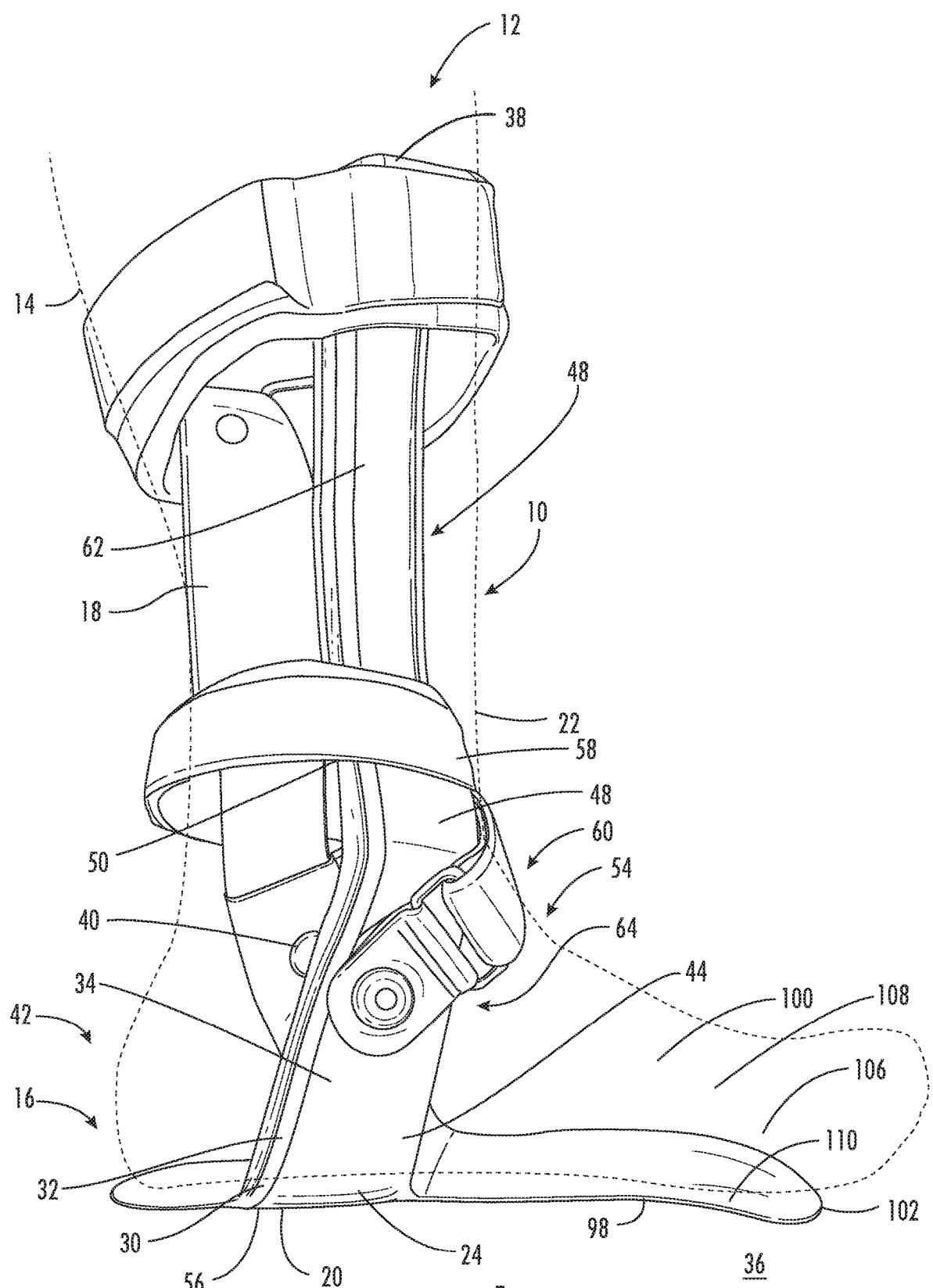
FIG. 1 is a right perspective view in partial phantom of the orthosis system of the present invention attached to a user's foot and leg in accordance with one or more aspects of the present disclosure.

Attention is now directed toward embodiments of the orthosis system and method for supporting a user's leg and foot. FIG. 1 is a right perspective view in partial phantom illustrating orthosis system (10) secured to a user's (12) leg (14) and foot (16), in accordance with one or more aspects of the present disclosure. As shown, the orthosis system (10) has an orthosis (18) having a foot section (20) coupled to a first riser (22) by a first coupler (24) and coupled to a second riser (26) by a second coupler (28). While the orthosis (18) may be constructed of any suitable material, in the preferred embodiment, the first coupler (24) is of a construction and configuration capable of coupling the foot section (20) to the first riser (22) in a manner that creates a resilient orthosis (18). Similarly, the second coupler (28) is also of a construction and configuration capable of coupling the foot section (20) to the second riser (26) in a manner that also creates a resilient orthosis (18). FIGS. 1-4.

In the preferred embodiment, the foot section (20), first coupler (24), second coupler (28), first riser (22) and second riser (28) are all integrally formed into a single, integral orthosis (18) from a composite (30), preferably a resin-impregnated fabric, and more preferably a carbon fiber fabric (32) reinforced with a polymer, such as an epoxy (34), in a manner such as that known in the art. Alternatively, known fabrics, such as fiberglass, cotton, polyester, and Kevlar may be used to form the orthosis (18). The carbon fiber fabric (32) may be of any desired thickness, construction, configuration, weave, or layering to provide the desired rigidity of the foot section (20), first riser (22) and second riser (28), and resilience of the first coupler (24) and second coupler (28). The first coupler (24) is constructed of a material sufficient to increase the bias of the orthosis (18) toward a predetermined starting orientation the more the first riser (22) is forced away from the starting orientation. Similarly, the second coupler (28) is constructed of a material sufficient to increase the bias of the orthosis (18) toward the starting orientation the more the second riser (26) is forced away from the starting orientation.

For example, a first layer of the carbon fiber fabric (32) may be laid on a second layer of the carbon fiber fabric (32) in a manner such that the weave of the first layer is oriented differently from the weave of the second layer to create, when the epoxy (34) is applied and hardened, a stronger composite (30) more resistant to deflection. Many layers of the carbon fiber fabric (32) may be oriented in this manner to create, when combined with the epoxy (34) a composite (30) with very specific deflection properties suitable for the purpose of a particular orthosis (18).

Whereas prior art orthoses may be constructed of plastic, one drawback of such devices is that the more portions of such prior art devices are deflected, the easier it is to deflect those portions. For example, in prior art devices, such as that described in United States Letters Patent 5,038,762, which is incorporated herein by reference, the more arms (2 and 3) are deflected away from the web (4), the weaker the connection between the arms (2 and 3) and the web (4) becomes and the easier it becomes to deflect the arms (2 and 3) even farther. This is undesirable in the preferred embodiment of the present invention. It is preferable in the present embodiment to provide a first riser (22) and a second riser (28) that become harder to deflect the more they are deflected relative to the normal positioning of the foot section (20). It is not, however, preferable to have a completely inflexible first riser (22) and a second riser (28), as such a construction would be uncomfortable for a user, and would not allow a small amount of deflection preferable to enhance ambulation and to rebound power to the user after the first riser (22) and second riser (28) are deflected and then released.

Accordingly, the composite (30) of the preferred embodiment is constructed of various layers of carbon fiber fabric (32), of various orientations of weave relative to one another and an epoxy (34) designed to allow the resulting orthosis to allow, in a normal walking, a user to deflect the foot section

(20) preferably between 1 and 20 degrees in a plantar direction relative to the first riser (22) and second riser (28), more preferably between 5 and 15 degrees, and most preferably about 9 to 11 degrees. The composite (30) is also of a construction and configuration designed to allow the resulting orthosis to allow, in a normal walking, a user to deflect the foot section (20) preferably between 0.5 and 8 degrees in a dorsal direction relative to the first riser (22) and second riser (28), more preferably between 1 and 6 degrees, and most preferably about 2 to 4 degrees.

Preferably, the orthosis system (10) is of a construction and configuration sufficient to control the valgus deviation of a user's foot during ambulation to ten degrees or less, and more preferably to a deviation of six degrees or less. The orthosis system (10) is of a construction and configuration sufficient to control the *varus* deviation of a user's foot during ambulation to ten degrees or less, and more preferably to a deviation of four degrees or less. The orthosis system (10) is of a construction and configuration sufficient to control the plantar flexion deviation of a user's foot during ambulation to forty degrees or less, and more preferably to a deviation of thirty degrees or less. The orthosis system (10) is of a construction and configuration sufficient to control the dorsal flexion deviation of a user's foot during ambulation to twenty degrees or less, and more preferably to a deviation of ten degrees or less.

The composite construction of the orthosis (18) allows for the user (12) to deflect the orthosis (18) somewhat during a normal stride. However, the more the user (12) tries to deflect the orthosis (18), the greater the orthosis (18) resists such deflection. Whenever the user (12) releases deformation pressure on the orthosis (18), the orthosis returns resistance power to the user (12) facilitating return of the user's foot (16) to its original position and completion of the stride. For example, if a user (12) wearing the orthosis system (10) on a right foot (16), tries to push that right foot (16) off the ground (36) as part of a normal stride, the orthosis (18) deflects the first riser (22) and second riser (28), relative to the foot section (20). Once the right foot (16) leaves the ground (36), the resiliency of the orthosis (18) forces the first riser (22) and second riser (28) back to their original position relative to the foot section (20).

Figure 3:
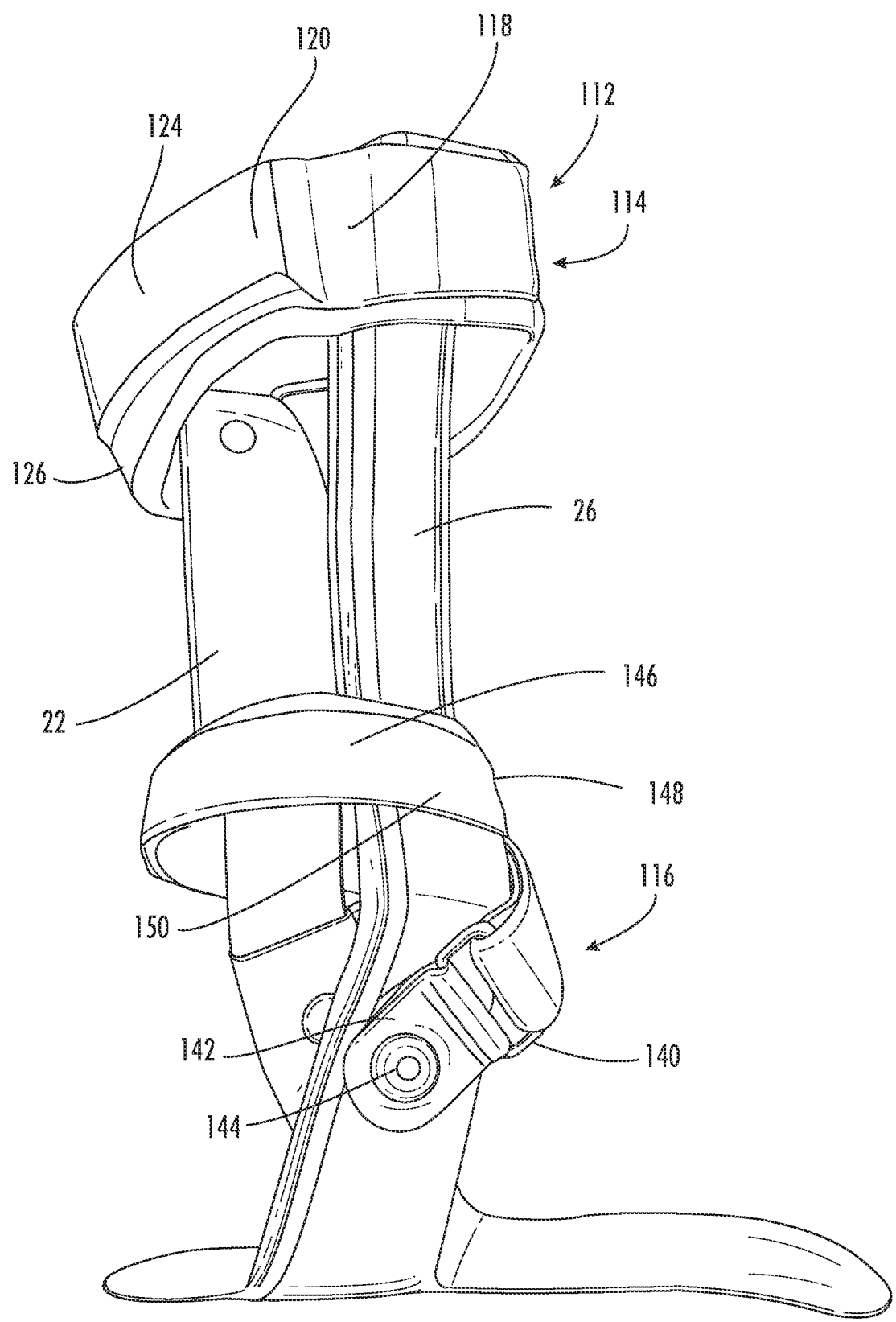
FIG. 3 is a right side elevation of the orthosis system of FIG. 1.
Figure 5:
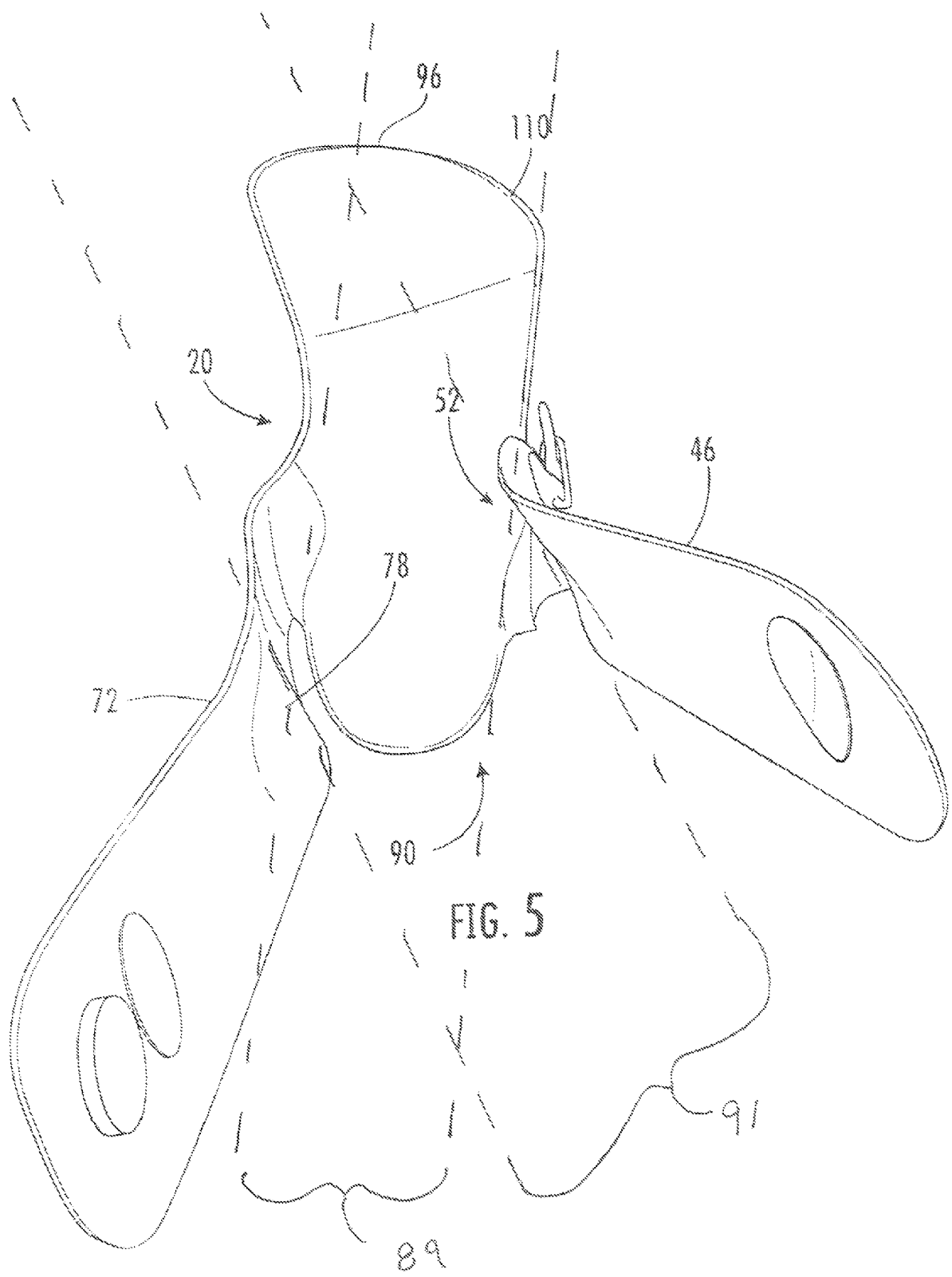
FIG. 5 is a top elevation of the orthosis system of FIG. 1.
Figure 6:
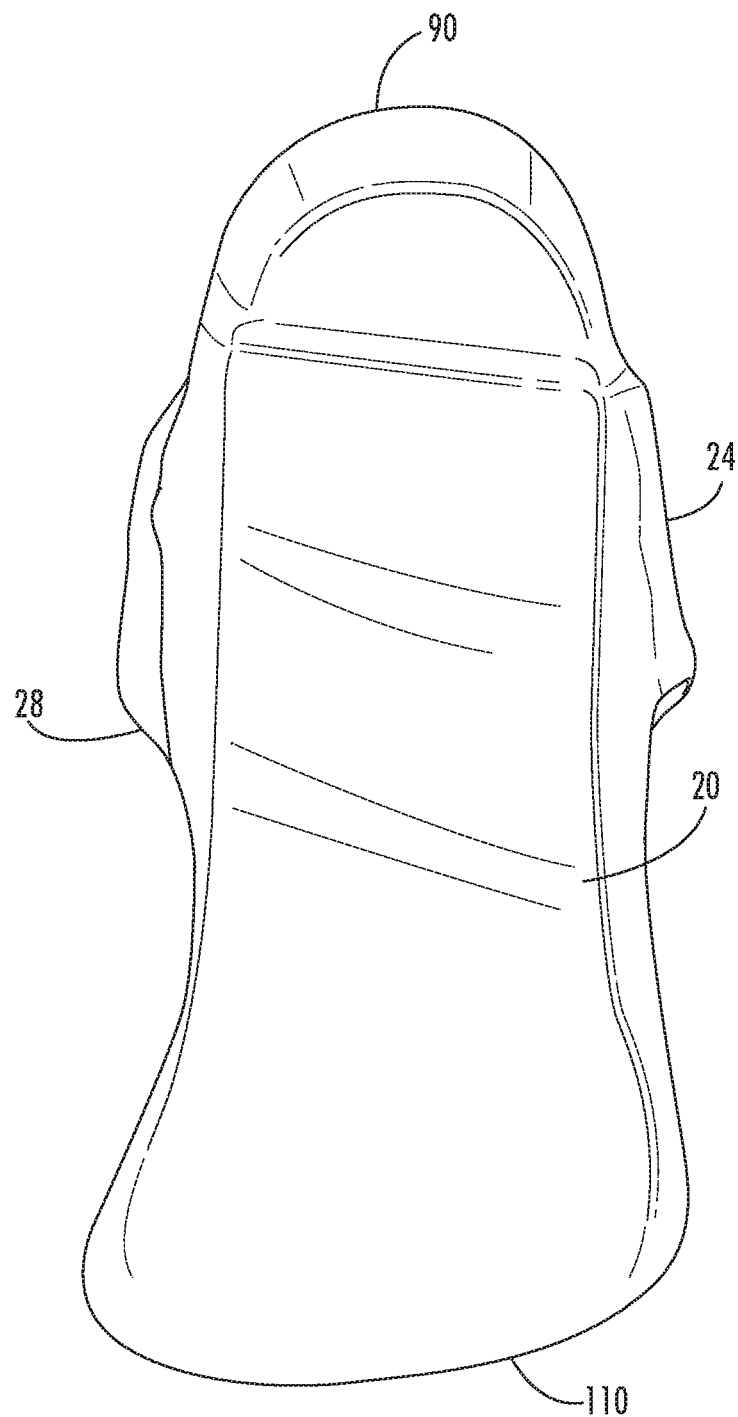
FIG. 6 is a bottom elevation of the orthosis system of FIG. 1.
Figure 7:
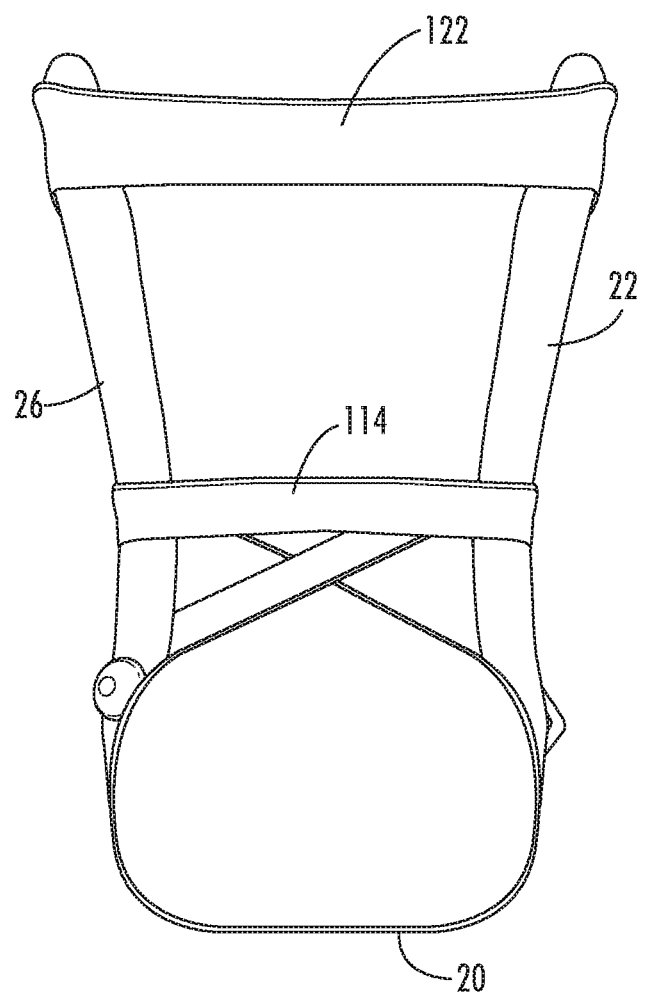
FIG. 7 is a rear elevation of the orthosis system of FIG. 1.

As shown in FIG. 1, a top (38) of the first riser (22) extends at least to a lateral malleolus (40) associated with an ankle (42) of the foot (16) of the user (12), more preferably to a point above the lateral malleolus (40) that is at least 50% of the distance the lateral malleolus (40) is above the ground (36) and most preferably to a point above the lateral malleolus (40) that is at least 100% of the distance the lateral malleolus (40) is above the ground (36). FIGS. 1, 3, and 5. The first coupler (24) angles a bottom (44) of the first riser (22) inward and forward relative to the foot section (20), with a slight clockwise twist (46), as viewed from above. The first riser (22) extends forward and inward until a portion (48) of the first riser (22) extends forward of the lateral malleolus (40). At this point (50), the first riser (22) begins to angle outward and rearward relative to the foot (16), with a slight counterclockwise twist (52). This construction of the first riser (22) follows the contour of the foot (16), initially angling forward and inward to secure the bridge (54) of the foot (16) before angling around the lateral malleolus (40) and then extending upward, outward, and rearward in a counterclockwise, helical, direction to secure the ankle (42) and leg (14). Preferably, at least a portion (56) of the bottom (44) of the first riser (22) is located rearward of the lateral malleolus (40), at least a portion (58) of a middle (60) of the first riser (22) is located forward of the lateral malleolus (40), and at least a portion (62) of the top (38) of the first riser (22) is located rearward of the lateral malleolus (40), with the first riser (22) thereby forming a forward-facing obtuse angle (64).

Figure 2:
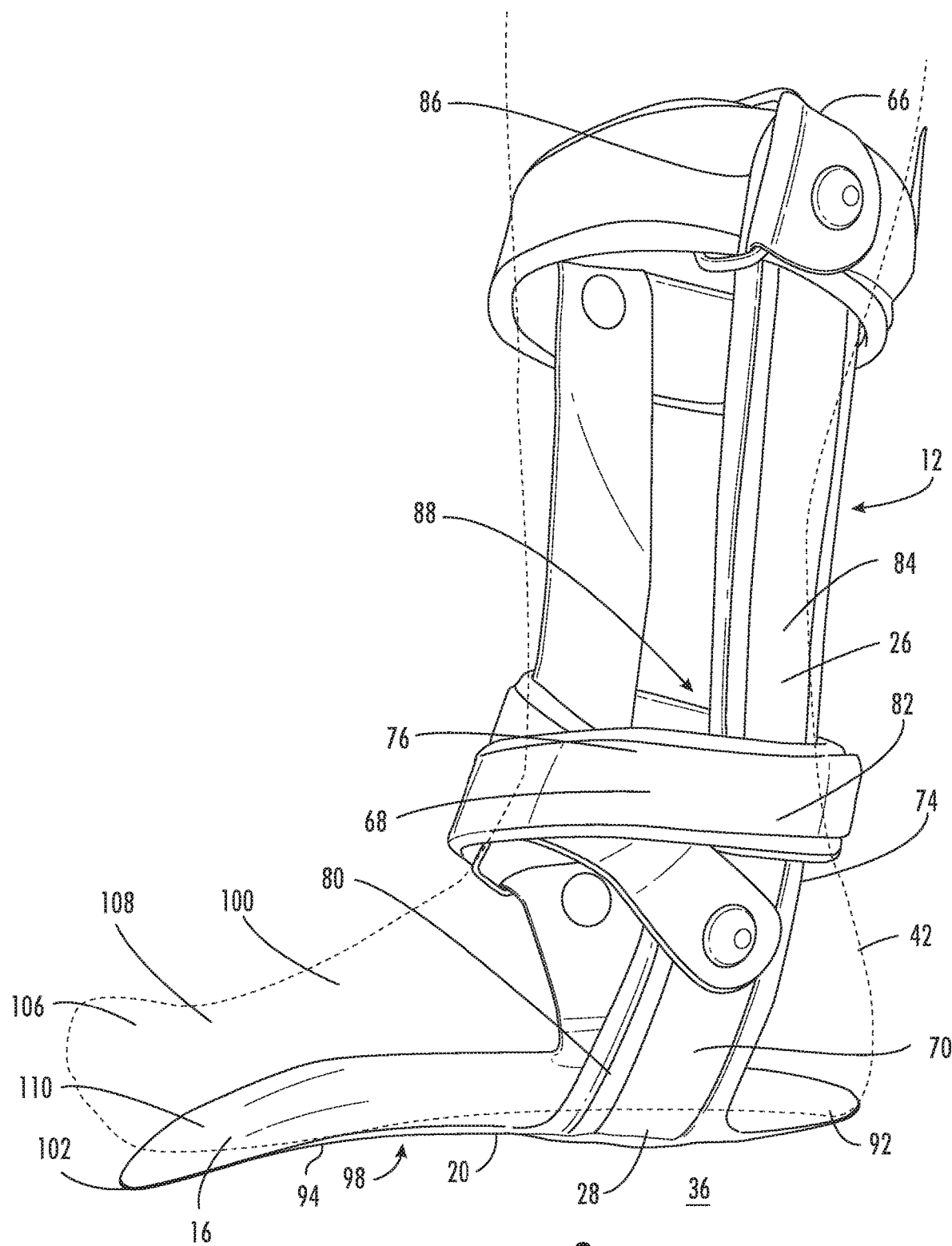
FIG. 2 is a left perspective view in partial phantom of the orthosis system of FIG. 1 attached to a user's foot and leg in accordance with one or more aspects of the present disclosure.
Figure 4:
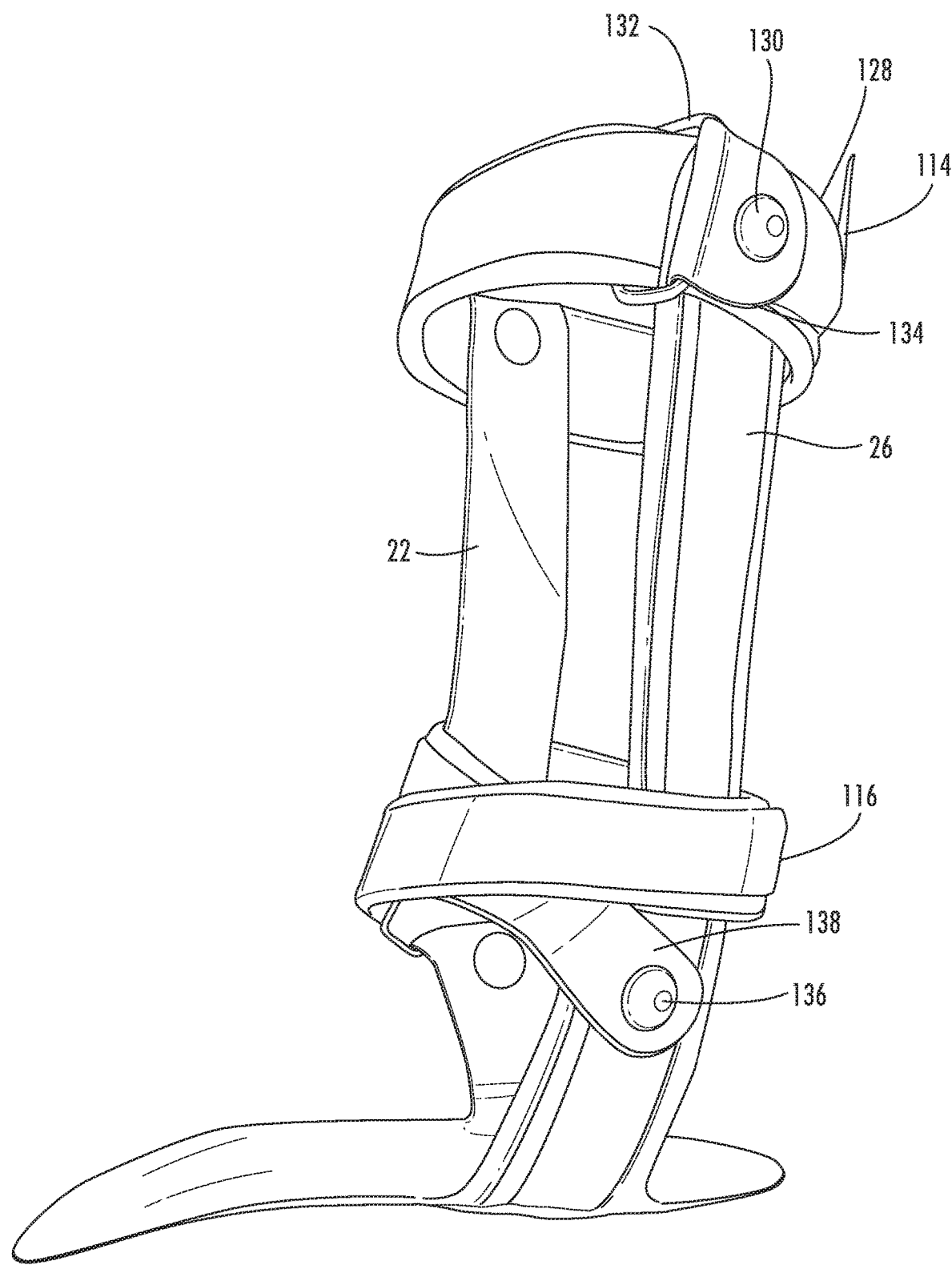
FIG. 4 is a left side elevation of the orthosis system of FIG. 1.

Similarly, as shown in FIG. 2, a top (66) of the second riser (26) extends at least to a medial malleolus (68) associated with the ankle (42) of the foot (16) of the user (12), more preferably to a point above the medial malleolus (68) that is at least 50% of the distance the medial malleolus (68) is above the ground (36) and most preferably to a point above the medial malleolus (68) that is at least 100% of the distance the medial malleolus (68) is above the ground (36). FIGS. 2, 4, and 5. The second coupler (28) angles a bottom (70) of the second riser (26) rearward and inward relative to the foot section (20), with a slight counterclockwise twist (72), as viewed from above. The second riser (26) extends rearward and inward until a portion (74) of the second riser (26) extends rearward of the medial malleolus (68). At this point (76), the second riser (26) begins to angle outward and forward relative to the foot (16), with a slight counterclockwise twist (78). This construction of the second riser (26) follows the contour of the foot (16), initially angling rearward and inward to secure the ankle (42) of the foot (16) before angling around the medial malleolus (68) and then extending upward, outward, forward, and in a counterclockwise, helical, direction to secure the ankle (42) and leg (14). Preferably, at least a portion (80) of the bottom (70) of the second riser (26) is located forward of the medial malleolus (68), at least a portion (82) of a middle (84) of the second riser (26) is located rearward of the medial malleolus (68), and at least a portion (86) of the top (66) of the second riser (26) is located forward of the medial malleolus (40), with the second riser (26) thereby forming a forward-facing acute angle (88). As described above and as shown in the drawings, the first riser (22) and the second riser (26) are oriented in at least a partial double helical orientation relative to one another along a line substantially normal to the foot section (20) and/or substantially along a center axis of the ankle (42) or leg (14).

The line of progression is designated as (89) in FIG. 5. As known in the art, the line of progression (89) is the line along which the user's (12) foot (16) moves when the user (12) is walking. (FIGS. 1 and 5). As shown in FIG. 5, the first riser (22) and second riser (26) extend in a double helical orientation around the user's (12) leg (14), with the first riser (22) extending sufficiently anterior of the user's (12) leg (14) to cross the line of progression (89) and such that the second riser extends sufficiently posterior of the user's (12) leg (14) to cross the line of progression (89). As shown in FIG. 5, the first riser (22) and second riser (26) define an opening (91) oblique to the line of progression (89).

As shown in FIGS. 1-2 and 5-6, the foot section (20) extends from a first end (90) positioned under a heel (92) of the foot (16), along the sole (94) of the foot (16) to a second end (96) preferably extending at least to a point (98) directly below at least one metatarsal (100) of the foot (16) and, more preferably, extending to a point (102) directly below multiple metatarsals (100) of the foot and, most preferably, to a point (104) directly below at least one phalanges (106) of the foot (16). At its widest, the foot section (20) preferably extends across at least half of the widest width (108) of the foot (16), more preferably extends across at least ninety percent of the widest width (108) of the foot (16), and most preferably extends across the widest width (108) of the foot (16). In this embodiment of the orthosis system (12), the number of layers of fabric (32) decreases from the first end (90) to the second end (96) of the foot section (20). This decrease in the number of layers provides the foot section (20) with a taper (110) from the first end (90) to the second end (96), and allows the first end (90) to flex more than the second end (96) of the foot section (20).

As shown in FIGS. 1-5, the orthosis (18) is secured to the user (12) by a user securement device (112) extending over the foot (16). The user securement device (112) is preferably a calf cuff (114) and an ankle cuff (116). Alternatively, a shell, such as that known in the art, constructed of plastic, leather, or similar material, may be provided over the orthosis (18) to maintain the orthosis (18) in place on a user's leg (14). Alternatively, the shell may be positioned between the user's leg (14) and the orthosis (18), and the orthosis (18) secured thereto. In other alternative embodiments, the shell may be a shoe, boot, or footwear insert holding the orthosis (18) in place.

In accordance with one aspect of the disclosure, the calf cuff (114) is a band (118) having first portion (120) provided with loop material (122) and a second portion (124) provided with hook material (126), such as that loop material and hook material well-known in the art of fabric hook-and-loop fastening systems. The band (118) may be elastic or otherwise resilient, and may be constructed of fabric, silicon, leather, or any suitable known material. The calf cuff (114) is pivotally secured on a first end (128), by a plastic rivet (130), such as those known in the art, to the second riser (26). A rectangular steel retention loop (132) is secured by a piece of fabric (134) that is also pivotably secured to the second riser (26) by the plastic rivet (130). The ankle cuff (116) is of a similar construction except whereas the calf cuff (114) is positioned above the lateral malleolus (40) and the medial malleolus (68), the ankle cuff (116) is positioned at least partially, and preferably fully below the lateral malleolus (40) and the medial malleolus (68). As shown, a first portion (138) of the ankle cuff (116) is pivotably secured to the second riser (26) by a plastic rivet (136) and a rectangular steel retention loop (140) of the ankle cuff (116) is pivotably secured by a piece of fabric (142) to the first riser (22) by another plastic rivet (144).

To secure the orthosis (18) to the user (12), the user (12) places a foot (16) into the orthosis (18). FIGS. 1-4 and 7. The user (18) then pulls a second portion (146) of the ankle cuff (116) forward and upward across the bridge (54) of the foot (16), wraps the ankle cuff (116) around the first riser (22), behind the leg (14), around the second riser (26), downward across the bridge (54) of the foot (16), through the retention loop (140), back upward across the bridge (54) of the foot (16), around the second riser (26), and secures hook material (148) on the second portion (146) into engagement with loop material (150) on the ankle cuff (116). To secure the calf cuff (114), the user (18) pulls the second portion (124) of the calf cuff (114) rearward behind the leg (14), around the first riser (22), forward in front of the leg (14), through the retention loop (132), forward in front of the leg (14), around the first riser (22), and secures the hook material (126) on the second portion (124) into engagement with the loop material (122) on the calf cuff (114). The calf cuff (114) and ankle cuff (116) may be any type of retainer for releasable securing the orthosis (18) to the user (12), used separately, or eliminated altogether. Alternatively, if the orthosis system (10) is going to be a permanent orthosis for the user (12), the user (12) may start out using both the calf cuff (114) and an ankle cuff (116), then eliminate the calf cuff (114) and an ankle cuff (116) over time.

Figure 8:
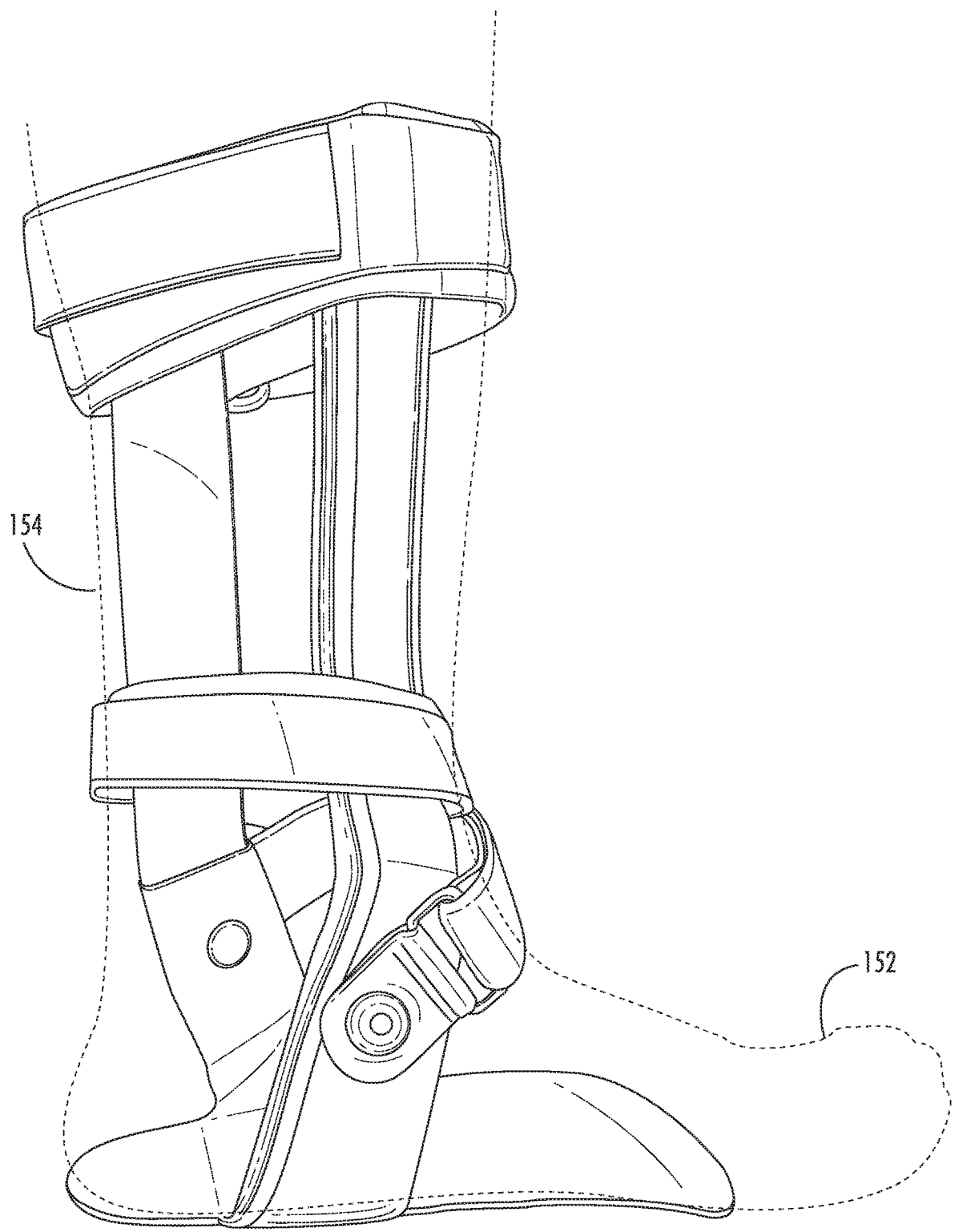
FIG. 8 is a side elevation in partial phantom of the orthosis system of FIG. 1 attached to a user's foot and leg and resisting the forward application of pressure against the orthosis system by a user's leg and the orthosis system returning pressure to the user's leg to stabilize the user and facilitate the user walking.

As shown in FIG. 8, once the user (12) has secured the orthosis (18) to the foot (16) and leg (14) and begins to walk, the when the user begins to walk, the user (12) pivots the foot (116) forward. As shown, the toes (152) bend and push off of the ground (36). The second end (90) of the foot section (20) contacts the ground (36) and begins to bow slightly as the orthosis (18) absorbs the force of the user (12) pressing the foot section (20) into the ground (36). This absorption of force allows the orthosis system (10) to limit further injury that may have resulted from the foot (16) or ankle (42) having to absorb this force. As the user (12) begins to lift the foot (16) off the ground (36), the foot section (20) unbows, releasing its rebound energy into lifting the foot (16) off the ground. Similarly, when the user (12) swings the foot (16) forward and begins to plant the foot (16) back on the ground, the first end (90) of the foot section (20) absorbs the shock of the foot placement, disbursing the force back out to buffer the impact of the user (12) continuing to rotate the foot (16) into contact with the ground to complete the step. The thickness, flexibility, construction, and configuration of the orthosis system (10) may be adjusted to precisely match the desired plantar flexation of the foot section (20) with the needs of the user (12). For long term users missing some or all of their calf muscles (154), the foot section (20) may be constructed to rebound the maximum amount of energy during ambulation. Conversely, if the user has sustained a lesser injury, requires less immobilization, or requires the use of muscle groups to improve recovery, the foot section (20) may be of a more flexible construction, rebounding less and returning less energy to the user during ambulation.

Figure 9:
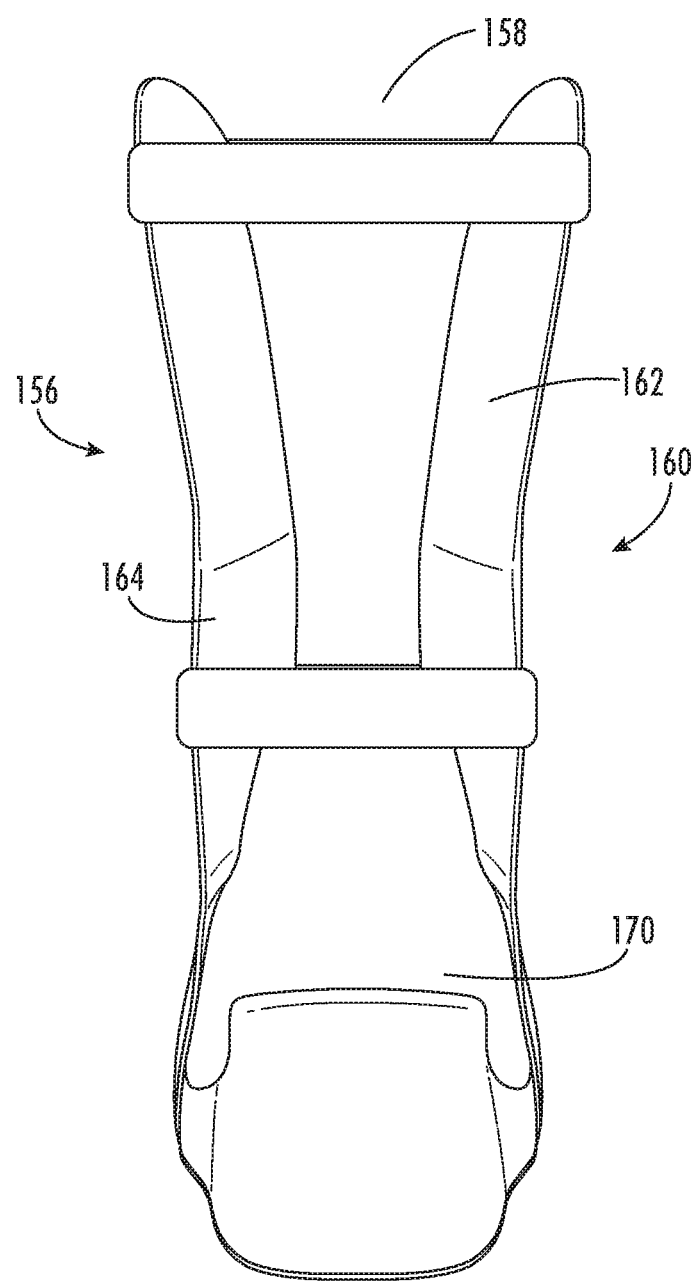
FIG. 9 is a rear elevation in partial phantom of the orthosis system of FIG. 1 attached to a user's foot and leg in accordance with one or more aspects of the present disclosure.
Figure 10:
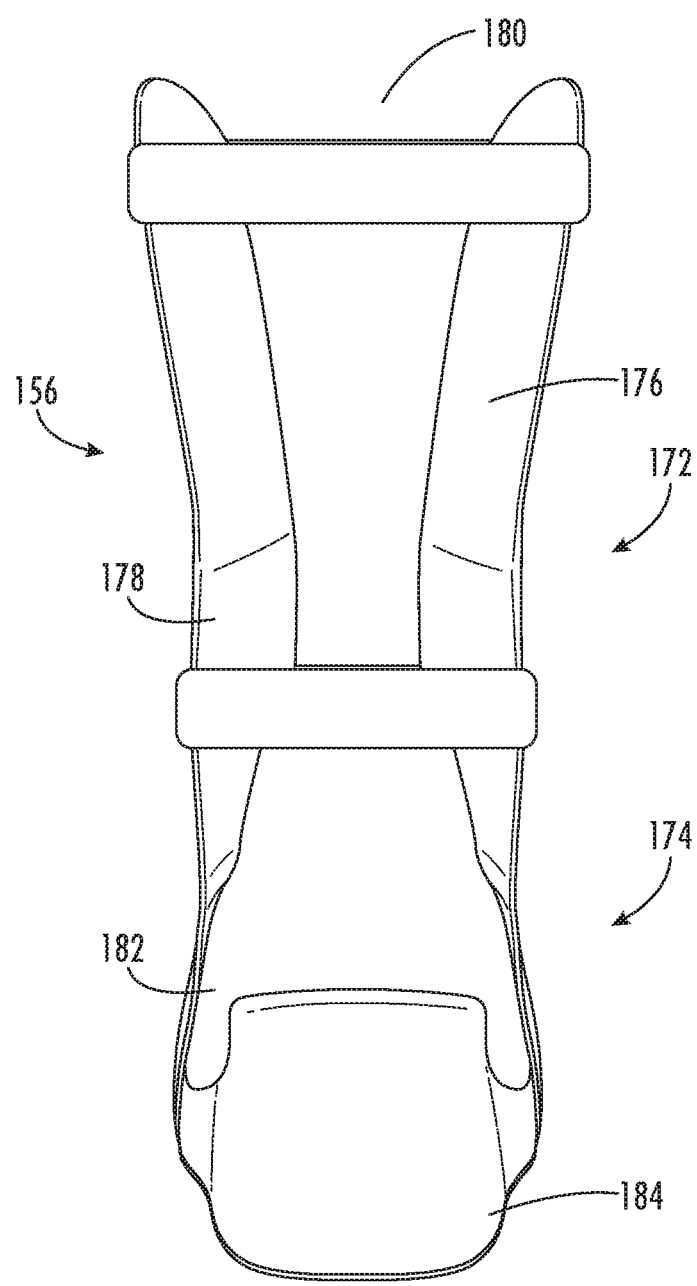
FIG. 10 is a rear elevation in partial phantom of the orthosis system of FIG. 1 attached to a user's foot and leg and resisting the lateral application of pressure against the orthosis system by a user's leg and the orthosis system returning pressure to the user's leg to maintain the stability of the user's leg and foot as the user walks.

As shown in FIG. 9, in accordance with one aspect of the disclosure, a modified embodiment of the orthosis system (156) may be used to ameliorate valgus or *varus* user deformities. For a user with a user (158) with a valgus deformity (160), the first riser (162) and second riser (164) may be modified so that instead of merely preventing the leg (166), ankle (168), and foot (170) from moving out of alignment, the first riser (162) and second riser (164) are of a construction and configuration biasing the leg (166), ankle (168), and foot (170) away from valgus deformity (160) toward a normal alignment. Similarly, as shown in FIG. 10, in accordance with another aspect of the disclosure, another modified embodiment of the orthosis system (172) may be used to ameliorate a *varus* deformity (174). In this embodiment, a first riser (176) and second riser (178) may be modified so that instead of merely preventing the leg (180), ankle (182), and foot (184) from moving out of alignment, the first riser (176) and second riser (178) are of a construction and configuration biasing the leg (180), ankle (182), and foot (184) away from valgus deformity (174) toward a normal alignment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Accordingly, the invention is not limited except as by the appended claims.

What is claimed is:

1. An orthosis for stabilizing a foot, which has metatarsals, and an ankle, which has a lateral malleolus and a medial malleolus, relative to a leg having a knee as the foot moves along a line of progression, the orthosis comprising:

(a) a resilient orthosis comprising:

(i) a forward foot section configured to extend to at least the metatarsals;
(ii) a lateral riser constructed of carbon fiber;
(iii) a lateral coupler coupling the lateral riser to the foot section;
(iv) a medial riser;
(v) a medial coupler coupling the medial riser to the foot section; and
(vi) a rearward foot section configured to extend rearward of the lateral riser and medial riser;
(b) wherein the lateral riser comprises:
  (i) a bottom having a front, a back, a rear edge, and a forward edge, wherein the bottom is configured to be located at least partially posterior of the lateral malleolus;
  (ii) wherein the lateral riser is configured to prevent *varus* deviation of the foot more than four degrees during ambulation;
  (iii) a middle configured to be located at least partially anterior of the lateral malleolus; and
  (iv) a top having a front, a back, a rear edge, and a forward edge, wherein the top is configured to be located at least partially posterior of the lateral malleolus;
(c) wherein the bottom of the lateral riser is configured to extend from the foot plate medial and anterior toward the lateral malleolus;
(d) wherein the top of the lateral riser is configured to extend lateral and posterior away from the lateral malleolus;
(e) wherein the top of the lateral riser is configured to extend anterior across the line of progression to store energy from the leg during dorsal foot flexion beyond zero flexion and return at least a portion of the energy to the leg during plantar foot flexion toward zero flexion during ambulation;
(f) wherein the lateral riser is configured to extend upward at least twice the height of the lateral malleolus;
(g) wherein the medial riser comprises:
  (i) a bottom having a front, back, a rear edge, and a forward edge, wherein the bottom is configured to be located at least partially anterior of the medial malleolus;
  (ii) wherein the medial riser is configured to prevent valgus deviation of the foot more than six degrees during ambulation;
  (iii) a middle configured to be located at least partially posterior of the medial malleolus; and
  (iv) a top configured to be located at least partially anterior of the medial malleolus;
(h) wherein the bottom of the medial riser is configured to extend from the foot plate lateral and posterior toward the medial malleolus;
(i) wherein the top of the medial riser is configured to extend medial and anterior away from the medial malleolus;
(j) wherein the top of the medial riser configured to extend posterior across the line of progression to store energy from the leg during plantar foot flexion beyond zero flexion and return at least a portion of the energy to the leg during dorsal foot flexion toward zero flexion during ambulation;
(k) wherein the medial riser is configured to extend upward at least twice the height of the medial malleolus;
(l) wherein the medial riser and lateral riser are configured to allow the forward foot section to deflect at least one degree, but no more than twenty degrees in a plantar direction relative to the medial riser during ambulation and are configured to allow the foot plantar flexion no more than thirty degrees during ambulation;
(m) wherein the medial riser and lateral riser are configured to allow the forward foot section to deflect at least one half of one degree, but no more than eight degrees, in a dorsal diction relative to the medial riser during ambulation and are configured to allow the foot dorsal flexion no more than ten degrees during ambulation; and
(n) wherein the medial riser and lateral riser define an opening, and are configured to direct the leg, along a line oblique to the line of progression.

2. The orthosis of claim 1, further comprising an ankle cuff coupled to the medial riser and the lateral riser.

3. The orthosis of claim 2, further comprising a calf cuff coupled to the medial riser and the lateral riser.

4. The orthosis of claim 1, wherein the medial riser, the lateral riser, and the foot section are integrally constructed of resin-impregnated fabric.

5. The orthosis of claim 1, wherein at least a portion of the medial riser and at least a portion of the lateral riser are oriented in at least a partial double helical orientation along a line normal to the foot section.

6. The orthosis of claim 1, wherein a widest portion of the foot section is configured to extend across at least half of the width of the foot.

7. The orthosis of claim 1, wherein the lateral riser is constructed of a material to increase the resilience of the orthosis toward a predetermined orientation the more the lateral riser is forced away from the predetermined orientation.

* * * * *

UNITED STATES PATENT AND TRADEMARK OFFICE
CERTIFICATE OF CORRECTION

| | |
|---|---|
| PATENT NO. | : 12,042,418 B2 |
| APPLICATION NO. | : 16/791439 |
| DATED | : July 23, 2024 |
| INVENTOR(S) | : Noel J. Chladek |

It is certified that error appears in the above-identified patent and that said Letters Patent is hereby corrected as shown below:

In the Claims

In Claim 1, Column 9, Line 40, before "back" and following "front," please insert --a--.

In Claim 1, Column 10, Line 7, before "configured" and following "riser" please insert --is--.

In Claim 1, Column 10, Line 24, please delete "diction" and insert therefor --direction--.

Signed and Sealed this
Tenth Day of September, 2024

Katherine Kelly Vidal
*Director of the United States Patent and Trademark Office*